United States Patent [19]

Fuzesi et al.

[11] 4,401,772

[45] Aug. 30, 1983

[54] METHYL GLUCOSIDE-AMINE-BASED POLYETHER POLYOLS AND POLYURETHANE FOAMS PREPARED THEREFROM

[75] Inventors: Stephen Fuzesi, Hamden; John G. Bayusik, Wallingford, both of Conn.

[73] Assignee: Olin Corporation, New Haven, Conn.

[21] Appl. No.: 368,614

[22] Filed: Apr. 15, 1982

Related U.S. Application Data

[62] Division of Ser. No. 218,871, Dec. 22, 1980, Pat. No. 4,359,573.

[51] Int. Cl.³ .................. C08G 18/14; C08G 18/50
[52] U.S. Cl. .................................. 521/167; 521/914; 536/17.2; 536/120
[58] Field of Search .......................... 521/167

[56] References Cited

U.S. PATENT DOCUMENTS

| | | | |
|---|---|---|---|
| 3,167,538 | 1/1965 | Kaiser et al. | 260/210 |
| 3,277,213 | 10/1966 | Fuzesi | 260/233.3 |
| 3,296,245 | 1/1967 | Kaiser et al. | 260/210 |
| 3,332,934 | 7/1967 | Booth et al. | 260/209 |
| 3,399,190 | 8/1968 | Fuzesi et al. | 260/233.3 |
| 3,402,170 | 9/1968 | Fuzesi et al. | 260/233.3 |
| 3,541,034 | 11/1970 | Fuzesi et al. | 260/2.5 |
| 3,763,111 | 10/1973 | Fijal | 260/77.5 AQ |
| 4,342,864 | 8/1982 | Fuzesi et al. | 521/167 |
| 4,366,265 | 12/1982 | Fuzesi et al. | 521/167 |

*Primary Examiner*—H. S. Cockeram
*Attorney, Agent, or Firm*—William D. Sabo

[57] ABSTRACT

A polyurethane foam which is a reaction product of a polyol reactant, an organic polyisocyanate reactant, a reaction catalyst and a foaming agent, said polyol reactant is made by (1) reacting starch with methanol in the presence of an acid catalyst to form a crude methyl glucoside reaction product; (2) then admixing this reaction product with an amine in the presence of a basic catalyst followed by (3) oxyalkylating this mixture with a lower alkylene oxide.

13 Claims, No Drawings

METHYL GLUCOSIDE-AMINE-BASED POLYETHER POLYOLS AND POLYURETHANE FOAMS PREPARED THEREFROM

This is a division, of application Ser. No. 218,871, filed Dec. 22, 1980, now U.S. Pat. No. 4,359,573.

This invention relates to a process for the preparation of methyl glucoside-amine-based polyether polyols, to the product resulting from the process, and to the use of these polyols in the preparation of polyurethane foams.

It is known in the art to use methyl-α-D-glucoside as a co-initiator in preparing a polyether polyol which in turn can be employed in preparing polyurethane foams. The use of methyl-α-D-glucoside-based polyols in the preparation of polyurethane foams has not become widespread, however, because of the generally high cost of relatively pure methyl-α-D-glucoside, and its rather limited availability.

One approach which has been followed in making the glucoside involves a costly two-step process. In the first step, an aqueous solution of starch is hydrolyzed with an acid catalyst, the resulting solution being heated to remove water to yield anhydrous dextrose. The resulting dextrose solution is then reacted, in a separate reaction, with methanol in the presence of an acid catalyst to liberate water and to form a glucoside product mixture from which methyl-α-D-glucoside is recovered. In carrying out this procedure, the numerous process steps required increase the cost of preparing methyl-α-D-glucoside to a relatively high level, and they also affect the yields adversely.

Another technique is disclosed in U.S. Pat. No. 3,296,245 issued to Kaiser and Fuzesi on Jan. 3, 1967. In this patent, there is disclosed a one-step process for preparing methyl-α-D-glucoside directly from starch. It is still necessary, however, to further employ rather costly separation techniques to recover methyl-α-D-glucoside from the reaction product.

It is, therefore, a primary object of the present invention to overcome the economic and other disadvantages in preparing polyether polyols from methyl-α-D-glucoside.

It is another object of the present invention to provide a novel process for preparing a crude methyl glucoside-amine-based polyether polyol.

It is a further object of the present invention to provide a novel crude methyl glucoside-amine-based product.

It is yet another object of the present invention to provide rigid polyurethane foams having highly satisfactory physical properties by utilizing the novel crude methyl glucoside-amine-based polyether polyols.

These and other objects of the invention will be apparent from the following detailed description thereof.

It has now been discovered that the objects of the invention may be accomplished by: reacting starch and methanol in the presence of an acid catalyst to form a crude methyl glucoside reaction product, the reaction being carried out at an elevated pressure and by reacting at least a stoichiometric proportion of the methanol with the starch; and admixing this crude product with an amine, and oxyalkylating the mixture with an alkylene oxide having from 2 to about 6 carbon atoms. The resulting polyether polyols may then be reacted with an organic polyisocyanate, a foaming agent and a catalyst to yield urethane foams having excellent physical properties.

The crude methyl glucoside-amine-based polyether polyol of this invention may be prepared from any starch, i.e., any compound having the formula $(C_6H_{10}O_5)_x$. These compounds are carbohydrates or polysaccharides which occur naturally in many plant cells. Typical starches which may be conveniently employed include potato starch, corn starch, chlorinated starches, rice starch, tapioca starch, wheat starch, mixtures thereof and the like. From an economic standpoint, potato starch and corn starch are preferred.

At least a stoichiometric proportion of methanol is reacted with starch to yield the crude methyl glucoside reaction product, but it is preferred to employ an excess of methanol. Preferably, the proportion of methanol is in the range between about 4 and about 20 moles of methanol per glucose unit weight of starch, but greater proportions may be employed if desired. When a ratio of less than about 4:1 is employed, the starch is not easily dissolved and an inert solvent is then necessary to obtain a significant rate of reaction.

Various other alcohols such as ethanol, allyl alcohol, benzyl alcohol, phenol and the like are not as effective as methanol in preparing the desired crude reaction product, although some product can be obtained.

The acid catalyst may be any inorganic or Lewis acid catalyst. Representative Lewis acid catalysts include, but are not limited to, boron trifluoride etherate, aluminum trichloride, ferric chloride, stannic chloride, titanium tetrachloride, etc., and mixtures thereof. Other suitable acid catalysts include inorganic acids such as sulfuric acid, phosphoric acid, hydrochloric acid, hydrofluoric acid, nitric acid and the like. The preferred catalyst is sulfuric acid. The acid catalyst is employed in a catalytic proportion to catalyze the reaction between starch and methanol. The proportion of catalyst is generally in the range between about 0.5 and about 5, and preferably between about 1 and about 3, percent by weight of the starch, but greater or lesser proportions may be utilized if desired.

The reaction may be carried out in an inert atmosphere, for example in an atmosphere of nitrogen, carbon dioxide or helium, but it is not necessary since the methanol atmosphere is generally satisfactory. The reaction is carried out under a pressure in the range between about 10 and about 200 p.s.i., and preferably between about 50 and about 90 p.s.i.

The reaction temperature will vary depending upon the degree of completion of the reaction, time of reaction, catalyst concentration, reactant proportions, and the like. However, generally the temperature is maintained in the range between about 80° and about 200° C., and preferably between about 100° and about 150° C.

The resulting crude reaction product contains as major components methyl-α-glucoside and methyl-β-D-glucoside, and it further includes other glucosides and carbohydrates. The relative proportions of glucoside compounds in the reaction product will vary depending upon the conditions employed in carrying out the reaction. Generally, however, the crude reaction product will contain from about 5 to about 95 percent of methyl-α-D-glucoside and from about 95 to about 5 percent of methyl-β-D-glucoside.

In the next step of the process of this invention, the crude methyl glucoside reaction product is admixed with an amine compound, the amine compound being employed in an amount of at least about 0.1 mole to about 10 moles per glucose unit weight of starch. An oxyalkylation catalyst is added; and then, while maintaining the temperature within the range of from about 100° to about 165° C., an alkylene oxide or a mixture of alkylene oxides, using random or step-wise addition, is introduced into the mixture. The resultant oxyalkylated product is a co-oxyalkylated product in that the alkylene oxide reacts with the methyl-α-D-glucoside, methyl-β-D-glucoside and other glucoside components of the crude methyl glucoside mixture and with the amine compound.

It is to be noted that the crude methyl glucoside reaction product will also usually contain excess methanol and water which is condensed during the starch-methanol reaction. It has been found desirable to reduce the content of these volatile components to no more than about 5, and preferably less than about 3, percent by weight of the crude reaction product prior to the oxyalkylation reaction. This removal of volatile components can be accomplished either before or after addition of the amine compound to the mixture.

In the process of the present invention, any suitable amine compound, including mixtures of compounds containing an amine, may be employed. Suitable amines include the following and mixtures thereof:

a. The primary aliphatic amines including mono-, di-, and triamines. These amines usually contain 1-8, and preferably 1-4, carbon atoms such as methylamine, ethylamine, n-propylamine, n-butylamine, n-amylamine, n-hexylamine, ethylene diamine, diaminopropane, diaminobutane, pentamethylene diamine, diethylene triamine, and mixtures thereof. Particularly preferred amines in this group are the diamines having 2-4 carbon atoms such as ethylene diamine.

b. The primary aromatic amines including mono-, di-, and triamines. Preferably these contain 6-8 carbon atoms such as aniline, methylaniline, phenylene diamine, toluene diamine and triaminobenzene. A particularly preferred amine in this group is toluene diamine which may be any isomer, such as 2,3-, 2,4-, and 2,6-toluene diamine, or a mixture of such isomers.

c. The alkanolamines, i.e., the aliphatic hydroxy amines. Usually each alkanol group in these amines contains from 2 to 5 carbon atoms. Illustrative are ethanolamine, diethanolamine, triethanolamine, the mono-, di-, and tripropanolamines, ethanolpropanolamine, diethanolpropanolamine, and the mono-, di-, and tributanolamines. Particularly preferred alkanolamines are those in which each alkanol group contains 2-3 carbon atoms such as the ethanolamines, the propanolamines and the ethanolpropanolamines.

The most preferred amines referred to above are selected from the group consisting of ethylene diamine, diaminopropane, toluene diamine, an ethanolamine such as mono-, di-, and triethanolamine, a propanolamine such as mono-, di-, and tripropanolamine, an ethanolpropanolamine such as monoethanolmonopropanolamine and diethanolpropanolamine, and mixtures of these amines.

Any suitable alkylene oxide, or a mixture of alkylene oxides, may be employed in the process of the present invention. However, it is preferable to utilize a lower alkylene oxide having between 2 and about 6 carbon atoms, such as ethylene oxide or propylene oxide or a mixture thereof.

A variety of conventional oxyalkylating catalysts may be used in carrying out the oxyalkylation reaction. However, it is preferred to employ an alkaline catalyst such as potassium hydroxide. The oxyalkylation reaction is allowed to proceed, usually using elevated temperatures, until a polyol product is obtained which has a hydroxyl number of about 30 to about 800, and preferably about 250 to about 600. The use of elevated temperatures and basic catalysts is conventional in the oxyalkylation art. Proper use of these should be apparent to those skilled in the art. The catalyst is generally employed in an amount of about 1 to about 5 percent by weight of the polyol. The oxyalkylation reaction is initially exothermic and cooling means are employed in order to maintain the reaction at the desired temperature.

In general, after completion of the oxyalkylation reaction, the basic catalyst is neutralized with a mineral acid, such as phosphoric acid, sulfuric acid or hydrochloric acid. The resultant polyol product is then recovered.

The crude methyl glucoside-amine-based polyols prepared in accordance with this process have a relatively low viscosity and excellent physical and chemical properties which make them suitable for use in the preparation of polyurethane foams. Either the so-called "one-shot method" or the "semiprepolymer technique" ("quasiprepolymer technique") may be employed in preparing polyurethane foams from the crude methyl glycoside-amine-based polyols.

Any organic polyisocyanate may be employed in the preparation of the polyurethane foams, including diisocyanates, triisocyanates, and polyisocyanates. Organic diisocyanates are preferred due to commercial availability, especially mixtures of isomers of toluene diisocyanate which are readily available commercially, such as the 4:1 mixture of the 2,4- and 2,6-isomers. Typical exemplificative isocyanates include, but are not limited to, the following: methylene-bis-(4-phenyl isocyanate), 3,3'-bitolylene-4,4'-diisocyanate, 3,3'-dimethoxy-4,4'-biphenylene diisocyanate, naphthalene-1,4-diisocyanate, hexamethylene diisocyanate, 1,4-phenylene diisocyanate, polymethylene polyisocyanate (such as may be purchased commercially under the trademark "PAPI"), etc. and mixtures thereof. The amount of isocyanate employed in the preparation of the polyurethane foams should be sufficient to provide at least about 0.7 NCO groups based on the number of hydroxyl groups present in the crude methyl glucoside-amine-based polyether polyol of the present invention, the number of hydroxyl groups in any additive employed and the number of hydroxyl groups employed in the blowing agent. An excess of isocyanate compound may be conveniently employed; and it is preferable, therefore, to employ about 1.0-1.25 NCO groups based on the number of hydroxyl groups.

The polyurethane foams are prepared in the presence of a foaming agent and a reaction catalyst. The foaming agent employed may be any of those known to be useful for this purpose, such as water, the halogenated hydrocarbons and mixtures thereof. Typical halogenated hydrocarbons include, but are not limited to, the following: monofluorotrichloromethane, difluorodichloromethane, 1,1,2-trichloro-1,2,2,-trifluoroethane, methylene chloride, chloroform, carbon tetrachloride, and mixtures thereof. The amount of blowing agent employed may be varied within a wide range. Generally, however, the halogenated hydrocarbons are employed in an amount from 1 to 50 parts by weight per 100 parts by weight of the crude methyl glucoside-amine-based polyether polyol of the present invention, and generally the water is employed in an amount of from 0.1 to 10 parts by weight per 100 parts by weight of the crude methyl glucoside-amine-based polyether polyol of the present invention.

The polyurethane foams are prepared in the presence of a catalytic amount of a reaction catalyst. The catalyst employed may be any of the catalysts known to be useful for this purpose, including tertiary amines and metallic salts. Typical tertiary amines include, but are not limited to, the following: N-methyl morpholine, N-hydroxyethyl morpholine, dimethylcyclohexylamine, triethylene diamine, triethylamine, trimethylamine and mixtures thereof. Typical metallic salts include, for example, the salts of antimony, tin and iron, e.g., dibutyltin dilaurate, stannous octoate, etc. and mixtures thereof. Generally speaking, the catalyst is employed in an amount from 0.1 to 5 percent by weight based on the crude methyl glucoside-amine-based polyether polyol of the present invention.

The polyurethane foams of the present invention may be prepared directly from the reaction between the crude methyl glucoside-amine-based polyether polyol and organic polyisocyanate in the presence of a foaming agent and a reaction catalyst. Optionally, various additives may be employed in the preparation of the polyurethane foams in order to achieve particular properties. Exemplificative of such additives include, but are not limited to, the following: halogen and phosphorus-containing reactive and non-reactive type additives to improve flame retardancy, monocarboxylic and polycarboxylic acid-based polyesters, monohydroxy compounds, polyhydroxy compounds, etc.

Some of the crude methyl glucoside-amine-based polyols employed in the present invention are characterized by a high room temperature viscosity. In these cases in order to prepare the polyurethane foam it will be necessary to apply heat in order to reduce the viscosity or to admix therewith a material, such as a polyether polyol, of lower viscosity. This may be conveniently accomplished by admixing a lower viscosity crude methyl glucoside-amine-based polyol with the higher viscosity crude methyl glucoside-amine-based polyol.

It is preferred in the preparation of the polyurethane compounds of the present invention to employ minor amounts of a surfactant in order to improve the cell structure of the polyurethane foam. Typical of such surfactants are the silicone oils and soaps. Generally up to 2 parts by weight of the surfactant is employed per 100 parts of methyl glucoside-amine-based polyether polyol.

Various additives can be employed which serve to provide different properties. e.g., fillers, such as clay, calcium sulfate, or ammonium phosphate may be added to lower cost and improve physical properties. Ingredients such as dyes may be added for color, and fibrous glass, asbestos, or synthetic fibers may be added for strength. In addition, plasticizers, deodorants and antioxidants may be added.

The process of the invention provides a relatively simple and practically attractive route to preparing methyl glucoside-amine-based polyether polyols. Furthermore, these polyols can be used in making rigid polyurethane foams having highly satisfactory physical properties. These objectives are achieved at minimum cost and without, at the same time, undermining the physical properties of the resulting polyols or of the polyurethane foams prepared therefrom.

The process of the present invention will be more readily apparent from a consideration of the following illustrative examples. In the following examples the starch employed contained associated therewith about 10 to 15 percent by weight of water. All parts and percentages are by weight unless indicated otherwise.

EXAMPLES 1–9

The hereinbelow outlined general procedure was followed in the preparation of crude methyl glucoside-amine-based polyols. The specific formulations are set forth in Tables I and II below.

A 2-gallon, stainless steel reactor was charged with the methanol, starch and sulfuric acid. The reactor was purged with nitrogen by alternately building pressure to 40 p.s.i. and venting to 5 p.s.i., four times, at room temperature. The system was heated to a temperature of 115°–125° C. At this temperature, the autogenous pressure of the reaction system should be 65–70 p.s.i.g. The temperature and pressure were maintained at 115°–125° and 65–70 p.s.i.g., respectively, for 1.5 hours. The mixture was cooled to 60°–70° C., and at this temperature, it was neutralized with 20 percent sodium hydroxide to a pH of 7.5–8.5.

The diethanolamine was then added to the mixture at 70°–80° C. The excess methanol and water were stripped from the mixture at 100°–110° C. using 10–20 Hg vacuum; water is stripped so that the mixture contains no more than 0.75 percent by weight of water. Potassium hydroxide was then added to the mixture in the amount of 0.5 percent by weight, based on the total weight of the glucoside and diethanolamine in the mixture, and this addition was followed by mixing for 0.5 hour. Thereafter, the alkylene oxide was added while maintaining the temperature at 110°–120° C. and the pressure at 25–60 p.s.i.g. during the addition. After addition of the alkylene oxide, the temperature was maintained at 110°–120° C. for 2 hours. The mixture was neutralized with 85 percent o-phosphoric acid in a molar ratio of o-phosphoric acid to potassium hydroxide of 0.5–1.0, and then stripped under vacuum at 110° C. before filtration.

Analysis of the product gave the properties indicated in Table III.

TABLE I

| Component | Example | | | | | | | | |
|---|---|---|---|---|---|---|---|---|---|
| (Grams) | 1 | 2 | 3 | 4 | 5 | 6 | 7 | 8 | 9 |
| Methanol | 192 | 192 | 128 | 192 | 192 | 192 | 192 | 192 | 192 |
| Starch.H$_2$O | 180 | 180 | 180 | 180 | 180 | 180 | 180 | 180 | 180 |
| Sulfuric Acid | 5 | 2.5 | 2.5 | 2.5 | 2.5 | 2.5 | 2.5 | 2.5 | 2.5 |

TABLE II

| Component | Example | | | | | | | | |
|---|---|---|---|---|---|---|---|---|---|
| (Moles) | 1 | 2 | 3 | 4 | 5 | 6 | 7 | 8 | 9 |
| Methyl Glucoside | 1.0 | 1.0 | 1.0 | 1.0 | 1.0 | 2.0 | 4.0 | 1.0 | 1.0 |
| Diethanolamine | 2.78 | 1.12 | 0.4 | 1.77 | 1.0 | 1.0 | 1.0 | 0.9 | 0.5 |
| Propylene Oxide | 14.1 | 8.1 | 5.5 | 7.85 | 9.9 | 15.1 | 25.7 | 7.2 | 7.57 |
| Ethylene | — | — | — | 3.48 | — | — | — | — | — |

TABLE II-continued

| Component | Example | | | | | | | | |
|---|---|---|---|---|---|---|---|---|---|
| (Moles) | 1 | 2 | 3 | 4 | 5 | 6 | 7 | 8 | 9 |
| Oxide | | | | | | | | | |

TABLE III

| Property | Example | | | | | | | | |
|---|---|---|---|---|---|---|---|---|---|
|  | 1 | 2 | 3 | 4 | 5 | 6 | 7 | 8 | 9 |
| Hydroxyl Number | 530 | 530 | 530 | 530 | 453 | 451 | 453 | 530 | 450 |
| Nitrogen, percent | 3.01 | 1.82 | 1.0 | 2.48 | 1.6 | 1.0 | 0.6 | 1.78 | 1.0 |
| Viscosity @ 25°, c.p.s. | 1,600 | 4,800 | 43,000 | 2,500 | 5,000 | 15,000 | 25,000 | 9,000 | 9,000 |

EXAMPLE 10

A rigid polyurethane foam was prepared from the product of Example 1 by admixing the following ingredients in the following proportions:

| Ingredient | Amount (Grams) |
|---|---|
| Liquid Product of Example 1 | 100 |
| Dow Corning ® 191 surfactant[1] | 2 |
| Dimethylcyclohexylamine catalyst[2] | 4 |
| Trichloromonofluoromethane blowing agent[3] | 37.4 |
| Polymethylene polyphenylisocyanate[4] | 145 |

[1] This is a silicone-glycol copolymer described in a 1977 Dow Corning bulletin, No. 22-476-77.
[2] This is a commercial product of Abbott Laboratories purchased under the trademark "Polycat-8".
[3] This is a commercial product of E. I. DuPont de Nemours and Company purchased under the trademark "R-11 B".
[4] This is a commercial product of Upjohn Company purchased under the trademark "PAPI-135" and having an approximate functionality of 2.6.

The mixture was allowed to foam and was cured at elevated temperature. The resultant rigid polyurethane foam had the physical properties listed in Table IV.

EXAMPLES 11–13

In the following Examples, the procedure of Example 10 was repeated except that the products of Examples 2–5 were used in Examples 12–15, respectively. The resultant rigid polyurethane foam had the physical properties listed in Table IV.

TABLE IV

|  | Example | | | |
|---|---|---|---|---|
|  | 10 | 11 | 12 | 13 |
| Liquid Product, Example | 1 | 2 | 3 | 4 |
| Cream, sec. | 11 | 14 | 19 | 8 |
| S. Gel, sec. | 48 | 54 | 61 | 27 |
| T. Free, sec. | 74 | 80 | 93 | 40 |
| Rise, sec. | 88 | 94 | 109 | 60 |
| Density, p.c.f. | 1.83 | 1.83 | 1.95 | 1.85 |
| Compressive Strength, p.s.i. | 26.95 | 34.85 | 39.60 | 23.00 |
| Compressive Strength, p.s.i. | 16.20 | 15.21 | 21.80 | 15.05 |
| K-Factor | 0.161 | 0.157 | 0.156 | 0.124 |
| Friability | 3.66 | 5.92 | 9.32 | 2.76 |
| Porosity | — | — | — | 81.59 |
| Dry Heat Age, @ 200° F. | 7.37 | 7.70 | 5.88 | 5.32 |
| Dry Heat Age, @ 230° F. | 23.07 | 14.60 | 9.00 | 15.09 |
| Humid Age, @ 158° F./100% RH | 17.81 | 12.20 | 10.57 | 16.01 |

What is claimed is:

1. In a polyurethane foam comprised of the reaction product of a polyol reactant, an organic polyisocyanate reactant, a reaction catalyst and a foaming agent, the improvement wherein said polyol reactant is prepared by:
   a. forming a crude methyl glucoside reaction product by reaction in the presence of a catalytic proportion of an acid catalyst,
   (1) starch and
   (2) methanol, said reaction being carried out at an elevated pressure and by reacting at least a stoichiometric proportion of said methanol with said starch, and
   b. admixing said crude methyl glucoside reaction product with an amine in the presence of a basic catalyst, maintaining said mixture at a temperature of from 100° to 165° C., and introducing into said mixture an alkylene oxide having between 2 and about 6 carbon atoms, said amine being employed in an amount of at least about 0.1 mole to about 10 moles per glucose unit weight of starch and being selected from the group consisting of an aliphtic amine having 1–8 carbon atoms, an aromatic primary amine having 6–8 carbon atoms, an alkanolamine in which each alkanol group contains 2–5 carbon atoms, and a mixture thereof.

2. The polyurethane foam of claim 1, wherein said starch is corn starch.

3. The polyurethane foam of claim 1, wherein said acid catalyst is sulfuric acid.

4. The polyurethane foam of claim 1, wherein said alkylene oxide is propylene oxide.

5. The polyurethane foam of claim 1, wherein said akylene oxide is a mixture of propylene oxide and ethylene oxide.

6. The polyurethane foam of claim 1, wherein said aliphatic amine is a diamine having 2–4 carbon atoms, said aromatic primary amine is toluene diamine, and said alkanolamine is an ethanolamine, a propanolamine or an ethanolpropanolamine.

7. The polyurethane foam of claim 1, wherein said amine is selected from the group consisting of ethylene diamine, toluene diamine, an ethanolamine, and a mixture thereof.

8. The polyurethane foam of claim 1, wherein said crude methyl glucoside reaction product contains an amount of volatile components, and further wherein the amount of said volatile components is reduced to no more than about 5 percent of said crude methyl glucoside reaction product prior to reaction with said alkylene oxide.

9. The polyurethane foam of claim 1, wherein said amine is an ethanolamine.

10. The polyurethane foam of claim 9, wherein said starch is corn starch.

11. The polyurethane foam of claim 10, wherein said acid catalyst is sulfuric acid.

12. The polyurethane foam of claim 11, wherein said alkylene oxide is propylene oxide.

13. The polyurethane foam of claim 11, wherein said alkylene oxide is a mixture of propylene oxide and ethylene oxide.

* * * * *

UNITED STATES PATENT AND TRADEMARK OFFICE
CERTIFICATE OF CORRECTION

PATENT NO. : 4,401,772

DATED : August 30, 1983

INVENTOR(S) : Stephen Fuzesi and John G. Bayusik

It is certified that error appears in the above-identified patent and that said Letters Patent is hereby corrected as shown below:

Column 2, line 54, "methyl-α-glucoside" should read --methyl-α-D-glucoside--.

Column 4, line 25, "glycoside" should read --glucoside--.

Column 8, line 4, claim 1a., "reaction" should read --reacting--.

Column 8, line 27, claim 1b., "aliphtic" should read --aliphatic--.

Signed and Sealed this

Twelfth Day of June 1984

[SEAL]

Attest:

GERALD J. MOSSINGHOFF

Attesting Officer       Commissioner of Patents and Trademarks